United States Patent [19]

Eggers

[11] Patent Number: 5,776,128
[45] Date of Patent: *Jul. 7, 1998

[54] HEMOSTATIC BI-POLAR ELECTROSURGICAL CUTTING APPARATUS

[75] Inventor: Philip E. Eggers, Dublin, Ohio

[73] Assignee: Hemostatic Surgery Corporation, Sausalito, Calif.

[*] Notice: The term of this patent shall not extend beyond the expiration date of Pat. No. 5,324,289.

[21] Appl. No.: 778,511

[22] Filed: Jan. 3, 1997

Related U.S. Application Data

[63] Continuation of Ser. No. 447,996, May 23, 1995, abandoned, which is a continuation of Ser. No. 257,734, Jun. 9, 1994, abandoned, which is a continuation of Ser. No. 877,703, May 1, 1992, Pat. No. 5,324,289, which is a continuation-in-part of Ser. No. 711,920, Jun. 7, 1991, abandoned.

[51] Int. Cl.$^6$ ................................................. A61B 17/36
[52] U.S. Cl. ............................. 606/48; 606/42; 606/46
[58] Field of Search ............................ 606/41–52

[56] References Cited

U.S. PATENT DOCUMENTS

| | | |
|---|---|---|
| 659,409 | 9/1900 | Mosher . |
| 1,586,645 | 6/1926 | Bierman . |
| 1,798,902 | 3/1931 | Raney . |
| 3,651,811 | 3/1972 | Hildebrandt et al. . |
| 3,685,518 | 8/1972 | Beurle . |
| 3,730,188 | 5/1973 | Ellman . |
| 4,092,986 | 6/1978 | Schneiderman . |
| 4,232,676 | 11/1980 | Herczog . |
| 4,271,838 | 6/1981 | Lasner et al. . |
| 4,353,371 | 10/1982 | Cosman . |
| 4,370,980 | 2/1983 | Lottick . |
| 4,492,231 | 1/1985 | Auth . |
| 4,590,934 | 5/1986 | Malis et al. . |
| 4,655,216 | 4/1987 | Tischer . |
| 4,671,274 | 6/1987 | Sorochenko . |
| 4,763,669 | 8/1988 | Jaeger . |
| 4,785,807 | 11/1988 | Blanch . |
| 4,848,337 | 7/1989 | Shaw et al. . |
| 4,887,612 | 12/1989 | Esser et al. . |
| 4,940,468 | 7/1990 | Petillo . |

(List continued on next page.)

FOREIGN PATENT DOCUMENTS

| | | |
|---|---|---|
| 2680314 | 2/1993 | France . |
| 342617 | 7/1972 | U.S.S.R. . |
| 575103 | 10/1977 | U.S.S.R. . |
| 2037167 | 7/1980 | United Kingdom . |
| 2066104 | 7/1981 | United Kingdom . |
| 2133290 | 7/1984 | United Kingdom . |
| 2161082 | 1/1986 | United Kingdom . |

OTHER PUBLICATIONS

J.D.K. Burton, *The Lancet*, "New Inventions" pp. 650–651, Oct. 24, 1959.

S.L. Corson, "Two New Laparoscopic Instruments: Bipolar Sterilizing Forceps And Uterine Manipulator", *Medical Instrumentation*, vol. 1, No. 11, Jan.–Feb. 1977.

The Cavitron Bipolar Coagulator, Cavitron Surgical Systems, 1979.

*Primary Examiner*—David M. Shay
*Attorney, Agent, or Firm*—Fish & Neave; Nicola A. Pisano

[57] ABSTRACT

A surgical instrument is described that incorporates bipolar electrodes on opposing shearing members for passing a high frequency current through the tissue for causing hemostasis of the tissue and for cutting the tissue. An electrically insulating material is interposed between the shearing members so that the electrodes are spaced apart from 0.002 to 0.050 inches and the current passes between the opposing electrodes through the tissue and not between the opposing shearing surfaces. The insulating material has a higher hardness than the opposing members to reduce wear of the insulation and provide a self-sharpening feature. Methods of simultaneously causing tissue and severing tissue are also provided. The use of a constant voltage high frequency power supply to deliver current to the tissue to cause hemostasis is described in conjunction with those methods.

16 Claims, 4 Drawing Sheets

U.S. PATENT DOCUMENTS

| | | |
|---|---|---|
| 4,969,885 | 11/1990 | Farin . |
| 4,985,030 | 1/1991 | Melzer et al. . |
| 5,009,656 | 4/1991 | Reimels . |
| 5,108,391 | 4/1992 | Flachenecker et al. . |
| 5,147,356 | 9/1992 | Bhatta . |
| 5,147,357 | 9/1992 | Rose et al. . |
| 5,151,102 | 9/1992 | Kamiyama et al. . |
| 5,312,434 | 5/1994 | Crainich . |
| 5,324,289 | 6/1994 | Eggers ............ 606/48 |
| 5,330,471 | 7/1994 | Eggers ............ 606/39 |
| 5,352,222 | 10/1994 | Rydell . |
| 5,391,166 | 2/1995 | Eggers ............ 606/39 |

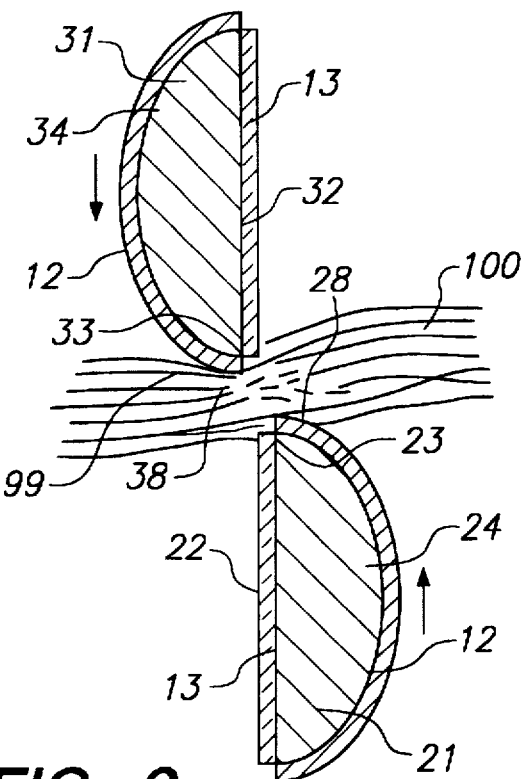
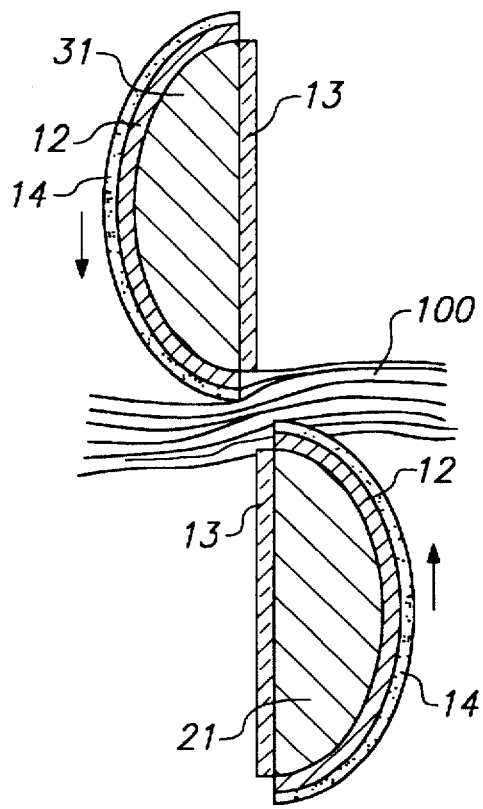
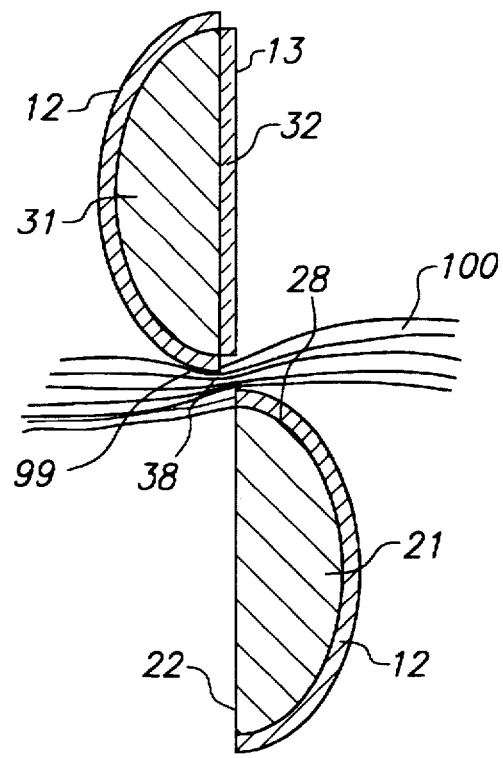
FIG. 3
FIG. 4
FIG. 5

HEMOSTATIC BI-POLAR ELECTROSURGICAL CUTTING APPARATUS

This is a continuation of application Ser. No. 08/447,996, filed May 23, 1995 entitled HEMOSTATIC BI-POLAR ELECTROSURGICAL CUTTING APPARATUS, now abandoned which is a continuation of application Ser. No. 08/257,734, filed on Jun. 9, 1994 now abandoned, which is a continuation of 07/877,703 now U.S. Pat. No. 5,324,289, filed on May 1, 1992, which is a continuation-in-part of 07/711,920,now abandoned, filed on Jun. 7,1991.

This invention relates to improved hemostatic electrosurgical instruments, and particularly to improved bi-polar electrosurgical instruments for severing and causing hemostasis of tissue.

BACKGROUND OF THE INVENTION

The control of bleeding during surgery accounts for a major portion of the time involved in an operation. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic surgical techniques are known for 20 reducing the bleeding from incised tissue prior to, during, and subsequent to incision. One such technique uses a heating element to transfer heat to the severed tissue to thermally reform collagen. Heat transferred from the instrument to the issue produces a thin collagenous film which seals over the severed blood vessels and capillaries, thus reducing bleeding. Localized application of heat reduces tissue necrosis or damage that may retard healing.

Electrosurgical techniques that pass a high frequency or radio frequency current through the patient's tissue between two electrodes for both cutting and causing hemostasis tissue also are known. The current passing through the tissue causes joulean (ohmic) heating of the tissue as a function of the current density and the resistance of the tissue through which the current passes. Such heating denatures the tissue proteins to form a coagulum that seals the bleeding sites.

Monopolar electrosurgical devices employ a small electrode at the end of a handle in the surgeon's hand and a large electrode plate beneath and in contact with the patient. only one of the two electrodes required to complete the electrical circuit it manipulated by the surgeon and placed on or near the tissue being operated on. The other electrode is the large plate beneath the patient. The electrosurgery power supply impresses high frequency voltage spikes of thousands of volts between these two electrodes, sufficient to cause an electric arcing from the small operating electrode the surgeon holds to the most proximate tissues, then through the patient to the large electrode plate beneath the patient. In the patient, the electrical current becomes converted to heat; hottest in the tissues immediately below the small hand-held electrode where the currents are most concentrated.

A principal disadvantage of monopolar electrocautery is that current flows completely through the patient. These high voltage electrical currents may arc from the small electrode to nearby non-targeted vital structures, or follow erratic paths as they flow through the patient's body, thus causing damage to tissues both near and at some distance from the electrode.

Another drawback of monopolar electrosurgical devices is the excessive tissue damage caused by the high voltage arc, including carbonization of the tissue, which compromises wound healing. Furthermore, monopolar devices typically create vision obscuring smoke, which must be evacuated from the surgical site.

In bipolar electrosurgical devices, two electrodes are closely spaced together and have the same surface area in contact with the tissue. The current flow is thus locally confined to the tissue that is disposed between and electrically connects the electrodes.

One difficulty encountered with prior art electrosurgical devices is that of controlling the current flow through the patient's tissue to obtain hemostasis in localized areas, without also heating and causing undesirable trauma to adjacent tissue. Although the introduction of bipolar electrosurgical devices has helped to localize current flow, previously known bipolar electrosurgical devices present difficulties in selectively applying the current flow.

For example, Hildebrandt et al. U.S. Pat. 3,651,811 and Soviet Union Patent Certificate 575,103 describe bipolar electrosurgical scissors having opposing cutting blades forming active electrodes. These devices enable a surgeon to sequentially coagulate the blood vessels contained in the tissue and then mechanically sever the tissue with the scissor blades. However, these devices apparently require the surgeon to cycle the power supplied to the electrodes during separate steps of obtaining hemostasis in the tissue and then cutting the tissue. In particular, these previously known devices require the surgeon to first energize the electrodes and grasp the tissue to cause hemostasis. Once the blood vessels contained within the tissue are coagulated, the electrodes are deenergized so that the scissor blades may be closed completely to sever the tissue mechanically. The scissors are then repositioned for another cut, and the power supply to the scissors cycled on and off again to congeal the tissue. Neither of these devices appear to permit the surgeon to maintain the electrodes in a continuously energized state, because the power supply would be shorted out or damaged if the blades were permitted to contact each other while energized.

Accordingly, a major drawback of previously known hemostatic bipolar electrosurgical cutting devices is that they have neither recognized the existence of, nor resolved the problem of, selectively delivering a current to obtain hemostasis at one location in the tissue, while simultaneously allowing already hemostatically heated tissue to be severed. It would therefore be desirable to provide a bipolar electrosurgical instrument that automatically and continuously adjusts the current delivery location so that it precedes the cutting point, without shorting the electrodes and interrupting the current providing hemostasis of the tissue.

Another drawback of previously known bipolar electrosurgical devices is the tendency for coagulum to build up on the electrode surfaces. Such buildup may impede the cutting ability of the device, cause sticking of the tissue to the device, and interfere with the surgeon's ability to manipulate the device at the surgical site.

Another related drawback is the tendency in previously known bipolar electrosurgical devices to experience some current leakage near the electrodes, which mat result in coagulum buildup on the non-active surfaces of the electrosurgical instrument as well.

It would therefore be desirable to provide an electrosurgical instrument wherein coagulum buildup on the surfaces of the instrument is reduced, thereby improving maneuverability of the instrument at the surgical site and reducing trauma to adjacent tissue.

Heretofore, no bipolar electrosurgical instrument for cutting and causing hemostasis of planar tissue areas has recognized or overcome the aforementioned problems. A continuing need for improved hemostatic electrosurgical scissors-like devices for simultaneously causing hemostasis in tissue and severing that tissue therefore exists.

SUMMARY OF THE INVENTION

In view of the foregoing, it is an object of the present invention to provide a bipolar electrosurgical scissors-like cutting instrument which simultaneously causes hemostasis of tissue and mechanically severs tissue in a continuous manner at a cutting point that advances along the cutting edges of the scissor members.

It is another object of the present invention to provide an electrosurgical scissors-like cutting instrument that eliminates the need for the surgeon to energize and deenergize the electrodes of the scissor members during the steps of causing hemostasis of the tissue and mechanically severing the tissue. The instrument constructed in accordance with the principles of this invention therefore reduces the likelihood that the electrodes may short circuit during cutting, thus permitting the instrument to be used for continuously hemostatically cutting tissue. The result is an instrument providing a smoother and more precise surgical cut than previously known devices, which permit hemostasis and cutting of discrete tissue sections in an intermittent, non-continuous, manner.

It is yet another object of the present invention to provide improved hemostatic electrosurgical scissors that reduce coagulum buildup and adherence of tissue to the working and non-working surfaces of the instrument.

It is still a further object of the present invention to provide methods for hemostatically severing tissue with an electrosurgical instrument, thereby reducing the number of steps required of the surgeon to employ the electrosurgical instrument in a continuous manner.

It is another object of the present invention to provide methods of using electrosurgical instruments that reduces coagulum buildup and sticking of tissue to the surfaces of the instrument.

These and other objects are accomplished in accordance with the principles of the present invention by providing a bipolar electrosurgical scissors-like instrument wherein each scissor member comprises an electrode for causing hemostasis of tissue and a shearing surface for mechanically severing the tissue. A layer of insulating material is disposed on at least one shearing surface of the scissors so that the electrically active portions of the scissor members do not contact each other at any point during operation of the instrument. Thus, current flows through tissue between the scissor members, but short circuits — which would terminate hemostasis — do not occur. With this arrangement, hemostasis and cutting occurs in a continuous manner along tissue disposed between the scissor blades.

In particular, an electrosurgical instrument constructed in accordance with the present invention comprises a scissors-like instrument including first and second scissor members. Each scissor member comprises a blade-like portion or shearing member having a shearing surface, a cutting edge and an exterior surface. The first and second scissor members are connected by connecting means so that the respective shearing surfaces move through a range of motion in a conventional scissors-like cutting action. That cutting action defines a cutting point that moves along the cutting edges of the respective shearing members through the range of motion, as is known. The instrument of the present invention further includes an electrode on each shearing member which is connected to a power supply that provides a high frequency current. An electrically insulating material is interposed between the electrodes so that the electrodes on the respective shearing members do not contact each other in the range of motion. The insulating material is disposed so that current passes between the electrodes of the respective shearing members distal to the cutting point, but not between the shearing surfaces.

In a first family of embodiments of the present invention, the first and second shearing members are made of an electrically conducting material so that they comprise, respectively, first and second electrodes. A first layer of electrically insulating material is disposed on at least one of the shearing surfaces, thereby forming the cutting edge and shearing surface of that shearing member. In these embodiments, the connecting means includes an electrically insulating material so that the shearing members are electrically isolated at the connecting means. The first layer of insulating material, whether disposed on one or both shearing surfaces, has a total thickness in the range of 0.002 to 0.050 inches, and preferably in the range of 0.003 to 0.007 inches.

To further achieve the advantages of the present invention, individual instruments of the first family of embodiments may include one or more of the following: a layer of material having a high electrical and thermal conductivity on one or both of the exterior surfaces of the shearing members; a second layer of insulating material disposed on the exterior surfaces of the shearing members, except for regions proximate the cutting edges; and a layer of abherent material disposed on the outermost tissue contacting portions of the instrument. These layers reduce coagulum buildup on the non-working surfaces of scissors, thereby reducing sticking and trauma to adjacent tissue. They also improve maneuverability of the instrument and enhance the surgeon's view of field, thereby enabling more precise surgical cutting.

A self-sharpening feature can be attained by employing a first layer of a first hardness on one of the shearing surfaces and a second layer of a second different hardness on the other shearing surface. Advantageously, the use of a harder material as one of the shearing surfaces provides for obtaining excellently mated cutting edges after a few cycles of operation and keeps the cutting edges sharp during repeated use.

In a second family of embodiments of the present invention, the first and second shearing members are made of a non-electrically conducting material, and the electrodes comprise a layer of electrically conducting material disposed on the exterior surfaces of each shearing member. In this arrangement, the electrically insulating material is comprised of the shearing members. The electrically conductive layers of the respective shearing members are spaced apart, at the cutting point, a distance in the range of from 0.002 to 0.050 inches, preferably 0.003 to 0.007 inches, as the cutting point moves through the range of motion. The layer of electrically conducting material on each shearing member may be comprised of an inner layer of a high electrical and thermal conductivity material and an outer layer of an oxidation resistant, high electrical and thermal conductivity material, the outer layer being superimposed in electrical contact over the inner layer.

Individual variations on instruments within the second family of embodiments may include an abherent layer covering the electrically conductive layer and a layer of electrically insulating material covering all of the electrically conductive layer except for a region of each shearing member proximate the cutting edge.

The present invention also includes methods of using bipolar electrosurgical instruments to simultaneously cause hemostasis in tissue while mechanically severing that tissue in a continuous manner, and without significant coagulum buildup or sticking. The methods include the steps of (a) providing first and second shearing members, each shearing member having a shearing surface, a cutting edge and an electrode, the shearing members connected together so that the shearing surfaces move in opposition through a range of motion in a scissors-like action that defines a cutting point moving along the cutting edges through the range of motion;

(b) connecting the electrodes to a power supply;

(c) selecting and maintaining a substantially constant voltage level output across the power supply, the voltage level output independent of the impedance of the load connected across the power supply;

(d) providing an electrically insulating material between the first and second electrodes so that the electrodes do not contact each other in the range of motion;

(e) placing the electrodes in electrical contact with tissue to be cut so that high frequency current passes between the electrodes and through the tissue distal to the cutting point, but not between the shearing surfaces; and (f) moving the first and second shearing members through the range of motion, thereby passing current through the tissue in a region distal to the cutting point, simultaneously causing hemostasis of the tissue and cutting the tissue at the cutting point.

The methods of the present invention include selecting suitable voltage and current ranges for employing the present invention. The methods further include the use of alternating current voltage waveforms having a crest factor — ratio of peak voltage to root-mean-square (RMS) voltage — near unity.

BRIEF DESCRIPTION OF THE DRAWINGS

The above and other objects and advantages of the invention will be apparent upon consideration of the following detailed description, taken in conjunction with the accompanying drawings, in which like reference numerals refer to like parts throughout, and in which:

FIG. 3 is a cross-sectional view taken along line 3—3 of FIG. 2

FIGS. 4–8 are cross-sectional views similar to that of FIG. 2 for various alternative embodiments of the present invention.

DETAILED DESCRIPTION OF THE INVENTION

Figure 1:
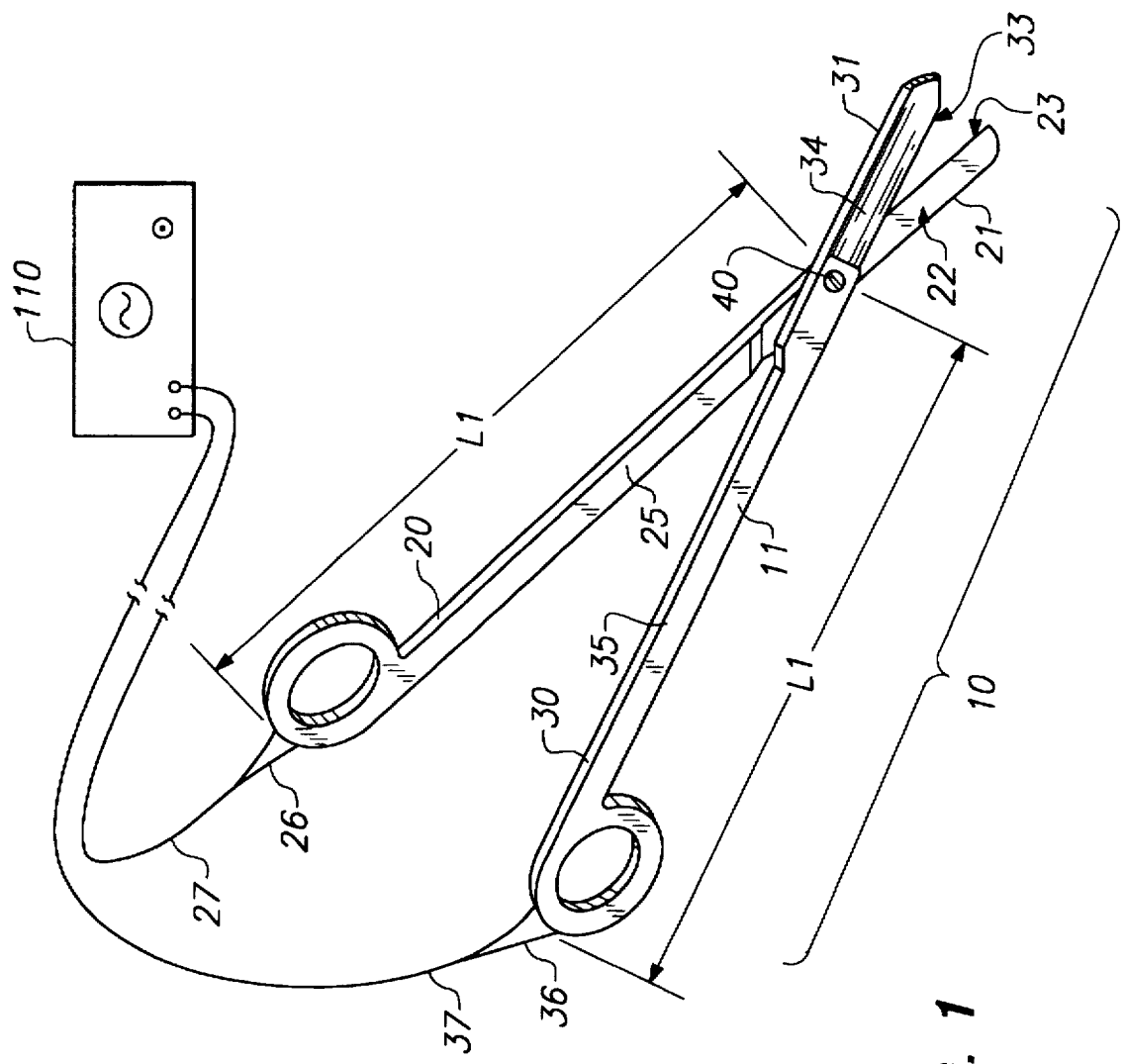
FIG. 1 is an elevation perspective view of a scissors constructed in accordance with a typical one of a family of embodiments of the present invention.
Figure 2:
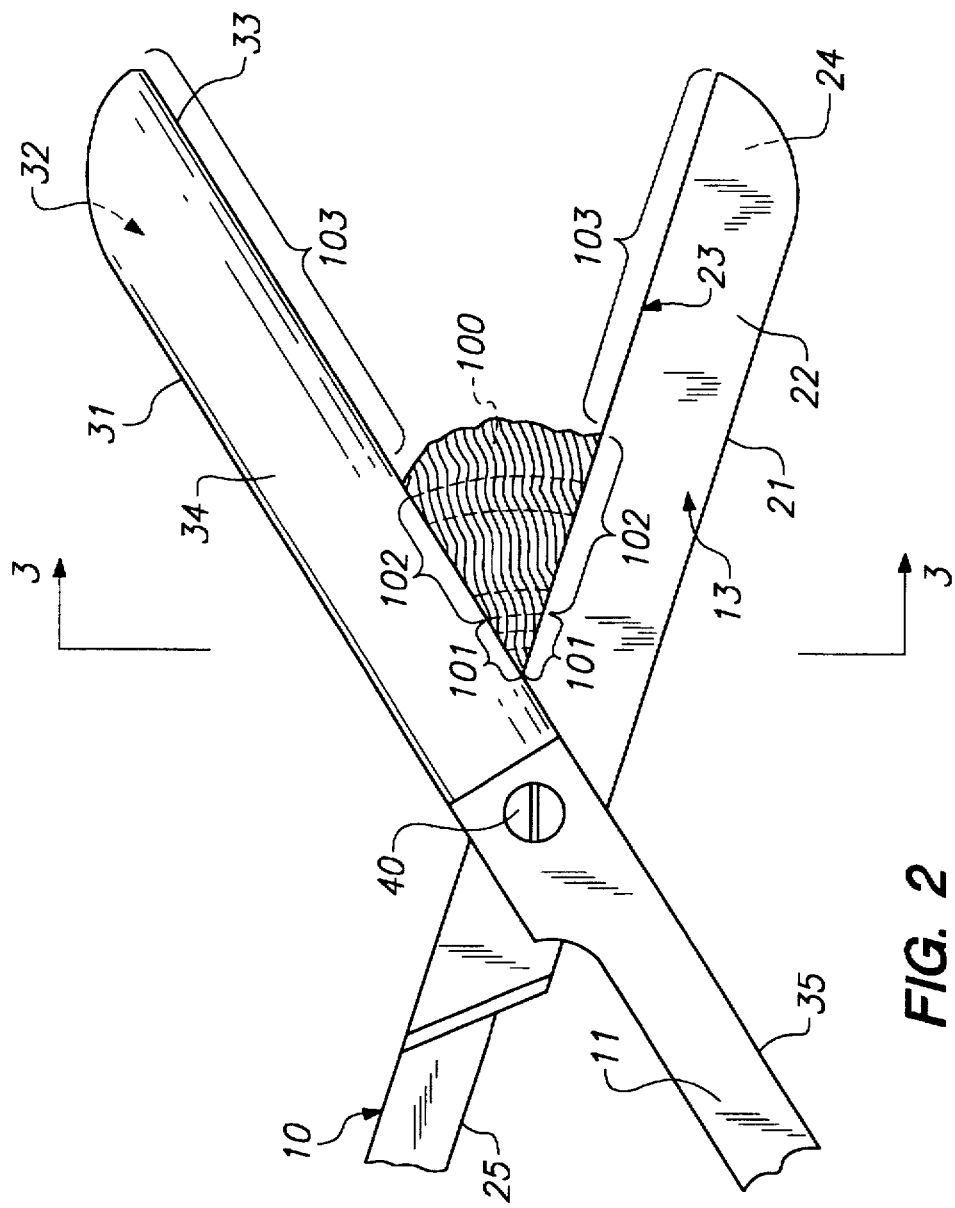
FIG. 2 is a side view of the scissors of FIG. 1, showing tissue disposed between the shearing members.

Referring to FIGS. 1–3, bipolar electrosurgical scissors 10 for simultaneously causing hemostasis in and shearing a patient's tissue 100 is described. Scissors 10 includes first scissor half 20 and second scissor half 30 pivotally connected by fastener 40. In a first family of embodiments constructed in accordance with present invention, scissor half 20 is made of an electrically conducting material and has at one end a first shearing member 21. Shearing member 21 forms a first electrode comprising shearing surface 22, cutting edge 23 and exterior surface 24. Scissor half 20 has, at the other end, support member 25, preferably configured with a thumb or finger hole for manipulating scissors half 20, and electrical connection 26 which connects the electrode to a conventional constant voltage power supply 10 via cable 27. Scissor half 30 is likewise made of an electrically conducting material and has at one end shearing member 31. Shearing member 31 forms a second electrode comprising shearing surface 32, cutting edge 33 and exterior surface 34. Scissors half 30 also has, at the other end, support member 35, preferably configured with a thumb or finger hole for manipulating scissors half 30, and electrical connection 36 which connects to power supply 110 via cable 37.

Power supply 110 may be a high frequency voltage source having a substantially constant voltage at selectable output levels. Such devices are described, for example, in U.S. Pat. No. 4,092,986 and 4,969,885. The power supply used in conjunction with the present invention preferably provides an output voltage level that is substantially constant at the user selected level, and independent of the electrical resistance encountered by the electrodes.

To reduce coagulum buildup on the working surfaces of the scissors, applicant has developed power supplies providing substantially constant voltage output that is independent of the load impedance, low source impedance and a alternating-current voltage waveform having a crest factor — the ratio of peak voltage to RMS voltage — near unity. These power supplies are described in commonly assigned U.S. Pat. No. 5,472,443, issued Dec. 5, 1995. (S-253). The present invention, when powered by such power supplies, has been observed to provide highly satisfactory hemostasis without arcing or charring of the tissue, and little coagulum buildup.

Scissor halves 20 and 30 are preferably made of a rigid, structural material capable of sustaining sharp scissors-like cutting edges 23 and 33, such as stainless steel or martensitic stainless steel. Alternatively, materials of high electrical and thermal conductivity, and structurally strong enough for shearing tissue, such as copper or copper alloys, may be used. Halves 20 and 30 are pivotally connected by fastener 40 in opposition so that shearing surfaces 22 and 32 and cutting edges 23 and 33 of the shearing members move in scissors-like opposition through a range of motion to sever tissue 100 placed therebetween.

Fastener 40 may be, for example, a screw or a rivet that electrically insulates scissor halves 20 and 30 at the pivot point. The fastener may be made of an insulating material, for example, polyamide or nylon. Alternatively, fastener 40 may comprise a combination of non-insulating and insulating materials, such as a stainless steel screw insulated from one or both scissor halves 20 and 30 by nylon bushings.

Scissor support members 25 and 35 have insulating coating 11 in regions $L_1$ to electrically insulate the support members from each other and from the surgeon using scissors 10. Insulating coating 11, which may comprise polyvinyl chloride, nylon, or other plastic insulating material, also may be applied to those areas of scissors 10 not used for cutting tissue.

As illustrated in FIG. 3, exterior surfaces 24 and 34 of the shearing members may have a coating 12 of a high electrical and thermal conductivity material, e.g., silver or copper, other than on their respective shearing surfaces 22 and 32. Coating 12 facilitates good electrical contact between exterior surfaces 24 and 34 and the tissue that comes into contact with those surfaces as shearing members 21 and 31 are moved relative to one another.

Coating 12 reduces localized heating of the exterior surfaces 24 and 34 of shearing members 21 and 31 by dissipating the heat throughout the thermally conducting surface area of the coating. Coating 12 also reduces the likelihood that joulean heating of shearing members 21 and 31 will occur, because any localized current flow is re-distributed over the entire coating 12. Consequently, coating 12 reduces thermal decomposition and sticking of blood and tissue to exterior surfaces 24 and 34 of scissors 10 during use.

A thin coating 13 of an electrically insulating material is disposed on each of shearing surfaces 22 and 32 to cover at least as much of those shearing surfaces as could contact each other within the full range of motion of scissor halves 20 and 30. Insulating coating 13 covers cutting edges 23 and 33 so that the cutting edges are electrically inactive and non-conducting.

As shown in FIG. 4, an alternative embodiment provides insulating coating 13 only on shearing surface 32 of shearing member 31. The other shearing surface 21 and cutting edge 23 remain electrically active, i.e., conductive. In this embodiment, electrical isolation between scissor halves 20 and 30 is achieved by the single layer of insulating material.

Insulating coating 13 allows the scissor halves forming the bipolar electrodes to move relative to each other so that current flows between exterior surface 24 of shearing member 21 and exterior surface 34 of shearing member 31, while ensuring that scissor halves 20 and 30 do not electrically contact each other. This configuration enables the cutting edges to contact each other to sever tissue while preventing short circuiting, which would impede simultaneous coagulation of the blood vessels extending through the tissue. Coating 13 substantially prevents current flow directly between opposing shearing surfaces 22 and 32 when the scissor halves are closed together. Rather, the current flows through the path of least resistance between the electrodes, i.e., through the tissue in direct contact with regions 28 and 38, respectively, of exterior surfaces 24 and 34 of the shearing members. This current flow is represented schematically by flux lines 99 shown in FIGS. 3 and 4.

The arrangement of the present invention confines current flow between regions 28 and 38 of exterior surfaces 24 and 34 to region 101 (see FIG. 2), from where cutting edges 23 and 33 contact each other to a point distal to the cutting point. That distal point is where either the tissue no longer forms an electrical connection between the electrode surfaces (region 102 of FIG. 2) or the spacing between halves 20 and 30 is sufficiently large that the current density is too low to cause significant joulean heating of the tissue (region 103 of FIG. 2).

It is therefore apparent that as scissors 10 is gradually closed, the cutting point moves along cutting edges 23 and 33 of shearing members 21 and 31 distally of fastener 40 and is preceded by region 101 in which a current flows from one scissor halve to the other to achieve hemostasis of the tissue. Thus, hemostasis occurs at a location just in advance of the cutting point while cutting edges 23 and 33 simultaneously sever the hemostatically heated tissue.

The embodiment of FIG. 4 permits an asymmetrical current flow between scissor halves 20 and compared to the embodiment of FIG. 3. Specifically, proximal to the cutting point, some current may flow from the uninsulated shearing surface to tissue in contact with that surface, through the tissue, and to an uninsulated portion of the other shearing member.

The applicant has determined that this asymmetry has no significant effect on the hemostatic cutting operation or the ability of the device to deliver current to the tissue relative to the embodiment of FIG. 3.

Electrically insulating layer 13 is preferably made of a material having a hardness that is greater or substantially greater than the steel or other electrically conducting material used to manufacture conventional scissors-like devices. For example, referring to the embodiment illustrated in FIG. 4, shearing members 21 and 31 may be made of a martensitic stainless steel, e.g., AISI 420. Insulating layer 13 comprises an inorganic electrically insulating material such as a glass, ceramic, nitride, boride or synthetic diamond. Depending upon the material selected, insulating layer 13 may be deposited on shearing surface 32 by conventional techniques, for example, plasma or flame-sprayed deposition. Applicant has obtained good results using ceramic materials such as alumina or zirconia.

The applied coating forms a non-conductive cutting edge for that shearing member and has a greater hardness than the steel substrate and the steel of opposing shearing member 21. consequently, as coating 13 rubs against the cutting edge 23 or shearing surface 22 of shearing member 21, steel shearing surface 22 and cutting edge 23 are mechanically ground or polished by the harder insulating material 13. Scissors 10 are therefore self-sharpening and remain sharp during continued use. Furthermore, the relatively lower hardness of steel cutting edge 23 will not wear or degrade the insulating characteristics or structure of the harder electrically insulating coating 13, thus providing a durable instrument.

The self-sharpening feature provided by the relatively greater hardness of insulating coating 13 also permits the use of less expensive materials for shearing members 21 and 31. For example, scissors 10 may be made of a material that may not retain a sharp cutting edge during repeated use absent the selfsharpening characteristic of the applied harder coating. This feature is particularly advantageous for constructing scissors 10 to be disposable, or in having disposable shearing members 21 and 31 that detach from their respective support members 25 and 35 (not shown).

Insulating coating 13 is deposited in a layer having a thickness in the range of 0.002 inches to about 0.050 inches, more preferably 0.003 to 0.007 inches. The applicant has determined that at thicknesses of 0.001 inch or less, the thickness of the insulating layer 13 is insufficient to prevent shorting of the electrodes. Insulating layer thicknesses above 0.002 inches and below 0.050 inches provide adequate hemostasis. It has been observed, however, that the greater the minimum distance between the proximate current conducting portions of the opposing electrodes in the region of current flow through the tissue, the longer the current path through the tissue and the more difficult it becomes to obtain the desired degree of hemostasis. For the ceramic insulating materials described, insulating layer thicknesses above 0.050 inches are believed to be too large for most practical applications.

Referring now to FIG. 5, another embodiment of the scissors of FIG. 1 is described. The scissors, constructed as described hereinbefore with respect to FIG. 3, have a coating 14 of an abherent material disposed on coating 12. The abherent material constituting coating 14 is capable of conducting high frequency current through its thickness and further reduces the sticking and accumulation of blood and tissue to exterior surfaces 24 and 34 of the shearing members. Suitable abherent materials for coating 14 include fluorocarbon material, conductor-filled fluorocarbon coatings or thin fluorocarbon coatings less than about 0.0002 inches thick (which may otherwise be electrically insulating), e.g., Vyolex 10002, available from Du Pont.

Figure 6:
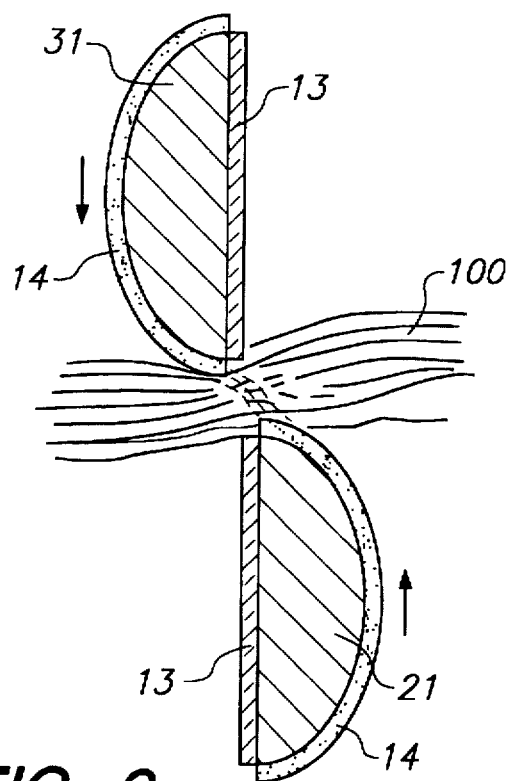

FIG. 6 shows yet another embodiment of the bipolar electrosurgical instrument of the present invention. This embodiment is similar to that of FIG. 4, except that exterior surfaces 24 and 34 of shearing members 21 and 31 are provided only with coating 14 of an abherent material and electrically conducting coating 12 is not applied.

Figure 7:
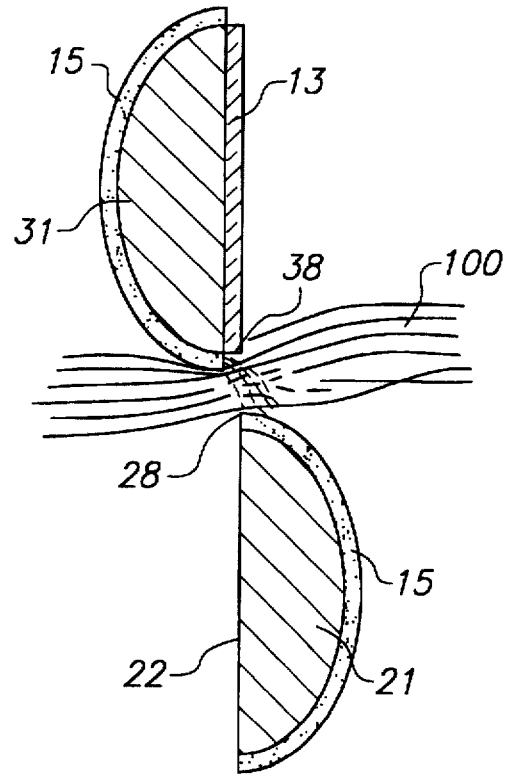

Referring now to FIG. 7, another alternative embodiment of the present invention is described. This embodiment is substantially the same as that described hereinbefore with respect to FIG. 4. This embodiments differs, however, in that instead of the electrically conductive coating 12 of the embodiment of FIG. 4, an electrically insulating layer 15 is disposed on exterior surfaces 24 and 34 of shearing members 21 and 31. Layer 15 is omitted from regions 28 and 38 immediately adjacent to cutting edges 23 and 33, respectively. Insulating layer 15 inhibits current flow to the tissue other than through regions 28 and 38 adjacent to cutting edges 23 and 33. Accordingly, heating of the tissue is localized to the region in and preceding the shearing region, thereby reducing joulean heating of tissue proximate to the portions of the exterior surfaces of shearing members 21 and 31 covered by insulating layer 15. Materials suitable for use in insulating layer 15 include aluminum oxide, fluorocarbons, polyamide and silicone based coatings.

Figure 8:
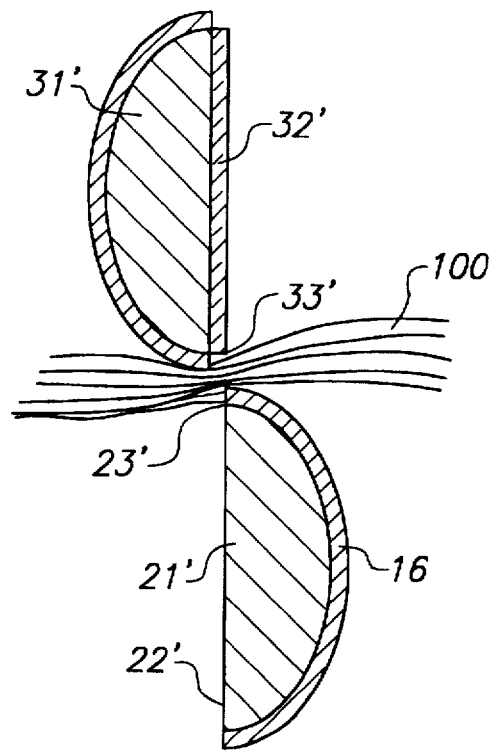

Referring to FIG. 8, an embodiment representative of a second family of embodiments constructed in accordance with the present invention is described, with similar components indicated by like-primed members. In this embodiment, which outwardly resembles the scissors of FIG. 1, opposing shearing members 21' and 31' are made of an electrically insulating material, e.g., a ceramic material such as zirconium oxide or aluminum oxide-based ceramics. The exterior surfaces of members 21' and 31', i.e., those portions other than the shearing surfaces 22' and 32' and cutting edges 23' and 33', have a coating 16 comprising a material of high electrical and thermal conductivity, e.g., copper, silver or nickel. Coating 16 thereby provides opposing electrodes for conduction of high frequency current through tissue between coatings 16 on exterior surfaces 24' and 34' of shearing members 21' and 31'. In this embodiment, coating 16 covers most of the exterior surface of shearing members 21' and 31' such that the current carrying sections closest to cutting edges 23' and 33' are no closer than 0.002 to 0.050 inches, and more preferably 0.003 to 0.007 inches. With the configuration of the embodiment of FIG. 8, shearing members 21' and 31' provide the desired insulating material between the electrodes.

EXAMPLES

Scissors in accordance with the embodiments illustrated in FIGS. 1–3 and 4 have been constructed of a martensitic stainless steel material (Grade AISI 420). Scissor halves 20 and 30 were nominally seven inches in length with shearing members 21 and 31 extending one and one-half inches beyond fastener 40. Shearing members 21 and 31 were 0.1 to 0.3 inches wide and 0.07 to 0.10 inches thick, the smaller dimensions being distal to the pivot. An insulating coating 13 was deposited on shearing surface 32 of shearing member 31 by plasma spraying alumina to a thickness in the range of 0.003 to 0.007 inches. Coating 13 was applied along the length of member 31 that contacts opposing member 21 in the full range of motion. Using conventional electroplating techniques, exterior surfaces 24 and 34 were provided with a coating 12 of a material having a high electrical and thermal conductivity comprising three layers:

- a first layer of copper, 0.002 to 0.003 inches thick, was deposited on all surfaces except the shearing surfaces;
- a second layer of nickel, 0.010 to 0.040 microinches thick, was then deposited on the copper layer and;
- a third layer of gold, 0.020 to 0.040 microinches thick, was deposited on the nickel layer. The nickel and gold layers provide an oxidation resistant protective outer layer for the thermally and electrically conductive sublayer of copper. Support members 25 and 35 included a coating 11 of an insulating material about 0.005 inches thick.

Experiments were performed on biological tissue and raw beefsteak using the above-described scissors in conjunction with an experimental power supply. The experimental power supply was operated at various selected constant frequencies in the range of 400 to 800 kHz and at selected levels providing a substantially constant voltage output level at the electrodes of the scissors in the range of 10 to 120 volts (RMS). This power supply had a low source impedance, and provided an alternating-current voltage waveform having a crest factor near one. The voltage waveform was maintained at a substantially constant level in the sense that the output volatage did not droop significantly at high loading.

The preferred operating range for the abovedescribed embodiment was found to provide a voltage at the electrodes of the instrument of 10–120 volts, more preferably 30–90 volts (RMS). The instrument operated satisfactorily throughout the above range of operating conditions, causing hemostasis of tissue and cutting tissue with minimal bleeding of that tissue. Accumulation of coagulated blood and tissue on the scissors was slight.

Frequencies below 100 kHz are known to affect the neuro-muscular systems of the patients, and may cause undesired stimulation. Applicant observed that frequencies above 800 kHz provided no advantage in operation and added cost to the power supply. While applicant believes that it would be possible to use higher frequencies, up to 2 MHz, the line losses in the cable connecting the electrosurgical instrument to the power supply would make use of such frequencies impractical.

Applicant observed that voltages (at the electrodes) below 10 volts (RMS) did not produce adequate joulean heating in the tissue to cause hemostasis. While prior art bipolar electrosurgical hemostatic teachings indicated that voltages above 120 volts (RMS) would be most desirable for achieving hemostasis of tissue, applicant observed that voltages above 120 volts (RMS) caused localized overheating of the electrodes and excessive accumulation of coagulum. Above 120 volts (RMS), rapid coagulum buildup necessitated frequent cleaning of the scissors, for example, every one to three cuts.

Applicant observed that the device according to FIG. 4, which has coating 13 on only one shearing surface, provides the same level of performance as devices having insulating layers on both shearing surfaces (when operated under the same conditions). For both embodiments, the amount of heating and depth of hemostasis on both sides of the cut tissue are substantially uniform. It will of course be understood by one skilled in the art that use of a voltage level greater than the above specified ranges may be suitable for causing hemostasis in tissue having higher impedance.

The scissors of the present invention also can be used for blunt dissection, for example, by spreading the scissors as they are advanced into tissue during the raising of a skin flap.

For such an embodiment, the blunt tips of the scissors are configured to cause hemostasis during the blunt dissection procedure. In such a procedure, the scissors are closed when inserted and then gradually opened, causing current flow outward of the cutting point, i.e., so that the dissected tissue hemostatically severed.

The various embodiments described herein are presented for purposes of illustration and not limitation, as the present invention can be practiced with surgical scissors-like instruments of any type or size having two cutting or shearing members movable with respect to one another. Thus, instruments constructed in accordance with the present invention may be adapted for use in cutting surface tissue, deep tissue and internal tissue, vessels, capillaries or organs, as may be required, for example, in microsurgery, macrosurgery, laparoscopy and other surgical procedures.

The present invention includes the method steps of employing an apparatus having shearing members that include electrodes, wherein operation of the apparatus simultaneously causes hemostasis of tissue and severs that tissue. As noted in the EXAMPLES provided above, applicant has observed that use of a scissors-like apparatus employing electrodes isolated by an intervening layer of insulating material at frequencies in the range of 400 to 800 kHz and 10 to 120 volts (RMS) provides satisfactory results.

The method of the present invention, suitable for use in a great variety of surgical procedures, comprises the steps of:

(a) providing first and second shearing members, each shearing member having a shearing surface, a cutting edge and an electrode, the shearing members connected together so that the shearing surfaces move in opposition through a range of motion in a scissors-like action that defines a cutting point moving along the cutting edges through the range of motion;

(b) connecting the electrodes to a power supply;

(c) selecting and maintaining a substantially constant voltage level output across the power supply, the voltage level output independent of the impedance of the load connected across the power supply;

(d) providing an electrically insulating material between the first and second electrodes so that the electrodes do not contact each other in the range of motion;

(e) placing the electrodes in electrical contact with tissue to be cut so that high frequency current passes between the electrodes and through the tissue distal to the cutting point, but not between the shearing surfaces; and (f) moving the first and second shearing members through the range of motion, thereby passing current through the tissue in a region distal to the cutting point, simultaneously causing hemostasis of the tissue and cutting the tissue at the cutting point.

Of course, it will be apparent to one skilled in the art that steps (a) and (d) described above can be combined by simply providing an apparatus as hereinbefore described, operation of the apparatus in the range 30 to 90 volts (RKS) will be desirable in many cases, depending upon the impedance of the tissue encountered during the surgical procedure.

The use of a power supply having a selectable substantially constant voltage level output that is independent of load impedance provides sufficient power to cause effective hemostasis. Use of constant voltage output levels lower than those generally used in previously known electrosurgical instruments reduces the power delivered to the electrodes when they are not in contact with tissue, i.e., open-circuited, and reduces the likelihood of generating a current arc when the electrodes are brought into contact with the tissue.

Use of a constant voltage level output that is independent of the load impedance inhibits excessive current flow through the tissue, as the tissue resistance increases during desiccation. Consequently, the depth of hemostasis obtained in the tissue can be more precisely controlled, and localized overheating of the electrodes better avoided. Reduced localized heating of the electrodes also inhibits coagulum buildup, which can both interfere with efficient hemostasis and impede maneuverability of the instrument.

One skilled in the art will appreciate that the present invention can be practiced by other than the described embodiments, and that the present invention is limited only by the claims which follow.

What is claimed is:

1. Apparatus for hemostatically cutting tissue, the apparatus comprising:

first and second scissor blades arranged to contact one another along a cutting length;

a layer of insulative material disposed for the cutting length to electrically isolate the first and second scissor blades from one another;

means for joining the first and second scissor blades together so that at least the first scissor blade moves relative to the second scissor blade in a scissors-like cutting motion, wherein the first and second scissor blades close together for shearing tissue located therebetween; and means for electrically coupling a high frequency alternating-current waveform to the first and second scissor blades.

2. The apparatus of claim 1, wherein the layer of insulative material has a thickness in a range of 0.002 to 0.050 inches.

3. Apparatus for hemostatically cutting tissue, the apparatus comprising:

a first shearing member having a first shearing surface and a first cutting edge first shearing member defining a first shearing plane and comprising a layer of electrically insulative material extending along the first shearing plane and a first layer of electrically conductive material extending along, and spaced apart from, the first shearing plane;

a second shearing member having a second shearing surface and a second cutting edge, the second shearing member defining a second shearing plane and comprising a second layer of electrically conductive material;

means for pivotally joining the first and second shearing members together so that the first and second shearing planes are co-planar;

wherein, when the first and second layers of electrically conductive material are coupled to a power source and the first shearing member is moved relative to the second shearing member in a scissors-like motion, a current flows from the first layer of electrically conductive material to the second layer of electrically conductive material through the tissue and the second shearing surface.

4. The apparatus as defined in claim 3 wherein the layer of electrically insulative material has a thickness selected in a range of 0.002 to 0.050 inches.

5. Apparatus for hemostatically cutting tissue, the apparatus comprising:

a first blade member comprising a composite of an electrically conductive material and an electrically insulative material, the first blade member having a portion defining a first shearing surface and a first cutting edge;

a second blade member comprising a composite of an electrically conductive material and an electrically insulative material, the second blade member having a portion defining a second shearing surface and a second cutting edge;

connection means for joining the first and second blade members together so that the first and second shearing faces oppose one another and the first cutting edge contacts the second cutting edge along a cutting length as the first blade member pivots relative to the second blade member in a scissors-like motion, wherein the electrically insulative material of the first and second blade members electrically isolates the first blade member from the second blade member along the cutting length.

6. The apparatus as defined in claim 5 wherein the electrically insulative material of the first blade member comprises a layer having a thickness selected in a range of 0.002 to 0.050 inches.

7. The apparatus defined in claim 5 wherein the electrically insulative material of the first blade member comprises a first thickness and the electrically insulative material of the second blade member comprises a second thickness and the sum of the first and second thicknesses is selected in a range of 0.002 to 0.050 inches.

8. A bipolar electrosurgical instrument for cutting and coagulating tissue comprising:

a first blade member comprising a first composite of an electrically conductive material and an electrically insulative material, the first blade member having a portion defining a first shearing surface, a first cutting edge, and a first electrode extending along, and spaced apart from the first shearing surface;

a second blade member comprising a composite of an electrically conductive material and an electrically insulative material, the second blade member having a portion defining a second shearing surface, a second cutting edge, and a second electrode extending along and spaced apart from the second shearing surface;

connection means for joining the first and second blade members together so that the first and second shearing faces oppose one another and the first cutting edge contacts the second cutting edge as the first blade member pivots relative to the second blade member in a scissors-like motion;

wherein the electrically insulative material of the first and second blade members electrically isolates the first electrode from the second electrode when the first and second cutting edges contact each other.

9. The apparatus of claim 8 wherein the electrically insulative material of the first blade member comprises a layer having a thickness selected in the range of 0.002 to 0.050 inches.

10. The apparatus of claim 9 wherein the electrically insulative material of the first blade member comprises a layer having a first thickness and the electrically insulative material of the second blade member comprises a layer having a second thickness and the sum of the first and second thicknesses is selected in a range of 0.002 to 0.050 inches.

11. Apparatus for hemostatically cutting tissue, the apparatus comprising:

a first blade member having a first shearing surface including a first cutting edge, and a first non-shearing surface, the first blade member comprising a thickness of electrically insulative material extending parallel to the first shearing surface and a first thickness of electrically conductive material extending parallel to, and spaced apart from, the first shearing surface, the thickness of the electrically insulative material and the first thickness of electrically conductive material forming a portion of the nonshearing surface;

a second blade member having a second shearing surface including a second cutting edge, the second blade member comprising a second thickness of electrically conductive material extending parallel to the second shearing surface;

means for pivotally joining the first and second blade members together so that the first and second shearing surfaces are co-planar, wherein, when the first and second thicknesses of electrically conductive material are coupled to a power source and the first blade member is moved relative to the second blade member in a scissors-like motion, a current flows from the first layer of electrically conductive material to the second layer of electrically conductive material through the tissue and across the first and second cutting edges.

12. The apparatus as defined in claim 11 wherein the second blade member comprises a thickness of electrically insulative material extending parallel to the second shearing surface interposed between the second shearing surface and the second thickness of electrically conductive material.

13. The apparatus as defined in claim 11 wherein the electrically insulative material of the first blade member comprises a layer having a thickness selected in the range of 0.002 to 0.050 inches.

14. A bipolar electrosurgical instrument for cutting and coagulating tissue comprising:

a first blade member comprising a first composite of an electrically conductive material and an electrically insulative material, the first blade member having a portion defining a first shearing surface, a first cutting edge and a first electrode;

a second blade member comprising an electrically conductive material, the second blade member having a portion defining a second shearing surface, a second cutting edge and a second electrode, the first and second cutting edges contacting one another along a cutting length;

connection means for joining the first and second blade members together so that the first and second shearing faces face one another and the first cutting edge contacts the second cutting edge along the cutting length as the first blade member pivots relative to the second blade member in a scissors-like motion, wherein the electrically insulative material of the first blade member electrically isolates the first electrode from the second electrode along the cutting length.

15. The apparatus of claim 14 wherein the electrically insulative material of the first blade member comprises a layer having a thickness selected in the range of 0.002 to 0.050 inches.

16. The apparatus of claim 14 wherein the electrically insulative.material of the first blade member comprises a layer having a first thickness and the second blade member further comprises a layer of electrically insulative material having a second thickness and the sum of the first and second thicknesses is selected in a range of 0.002 to 0.050 inches.

* * * * *